United States Patent
Baumgarte et al.

(10) Patent No.: US 10,315,352 B2
(45) Date of Patent: Jun. 11, 2019

(54) DEVICE AND METHOD FOR TRANSPORTING PREFORMS IN THE REGION OF A BLOW-MOLDING MACHINE

(71) Applicants: KHS Corpoplast GmbH, Hamburg (DE); KHS GmbH, Dortmund (DE)

(72) Inventors: Rolf Baumgarte, Ahrenburg (DE); Michael Linke, Hamburg (DE); Frank Lewin, Tangstedt (DE); Dirk Schenk, Neu-Bamberg (DE)

(73) Assignees: KHS Corpoplast GmbH, Hamburg (DE); KHS GmbH, Dortmund (DE)

( * ) Notice: Subject to any disclaimer, the term of this patent is extended or adjusted under 35 U.S.C. 154(b) by 248 days.

(21) Appl. No.: 15/504,775

(22) PCT Filed: Aug. 11, 2015

(86) PCT No.: PCT/EP2015/001650
§ 371 (c)(1),
(2) Date: Feb. 17, 2017

(87) PCT Pub. No.: WO2016/029997
PCT Pub. Date: Mar. 3, 2016

(65) Prior Publication Data
US 2017/0252960 A1 Sep. 7, 2017

(30) Foreign Application Priority Data

Aug. 28, 2014 (DE) .................. 10 2014 012 528

(51) Int. Cl.
| | |
|---|---|
| B29C 49/80 | (2006.01) |
| B29C 49/42 | (2006.01) |
| B29C 49/06 | (2006.01) |
| B29C 49/08 | (2006.01) |
| B29C 49/78 | (2006.01) |
| G01N 21/90 | (2006.01) |

(52) U.S. Cl.
CPC .............. *B29C 49/80* (2013.01); *B29C 49/06* (2013.01); *B29C 49/08* (2013.01); *B29C 49/42* (2013.01);
(Continued)

(58) Field of Classification Search
CPC . B29C 49/80; B29C 49/4252; B29C 49/4205; G01N 21/9081
See application file for complete search history.

(56) References Cited

U.S. PATENT DOCUMENTS

| | | | |
|---|---|---|---|
| 6,575,305 B1* | 6/2003 | Casagrande | B07C 5/3404 198/455 |
| 2010/0255142 A1* | 10/2010 | Brown | B29C 49/4205 425/534 |
| 2018/0015657 A1* | 1/2018 | Linke | B29C 49/78 |

FOREIGN PATENT DOCUMENTS

| | | |
|---|---|---|
| DE | 3990331 T1 | 2/1991 |
| DE | 19737527 A1 | 3/1999 |

(Continued)

*Primary Examiner* — Robert B Davis
(74) *Attorney, Agent, or Firm* — Rankin, Hill & Clark LLP

(57) ABSTRACT

The invention relates to devices and to methods for transporting preforms in the region of a blow-molding machine, in particular a sorting device (10) for transporting preforms (20) composed of a thermoplastic material in the region of a blow-molding machine for the blow-molding of containers, comprising a transportation wheel (12), which has a plurality of accommodating recesses (18) for accommodating and conveying the preforms (20), which accommodating recesses are arranged on the circumference of the transportation wheel in such a way that the accommodating recesses are distributed in the circumferential direction, a guide collar (16), which extends circumferentially around the transportation wheel (12) in some regions in such a way that the
(Continued)

Figure 1:
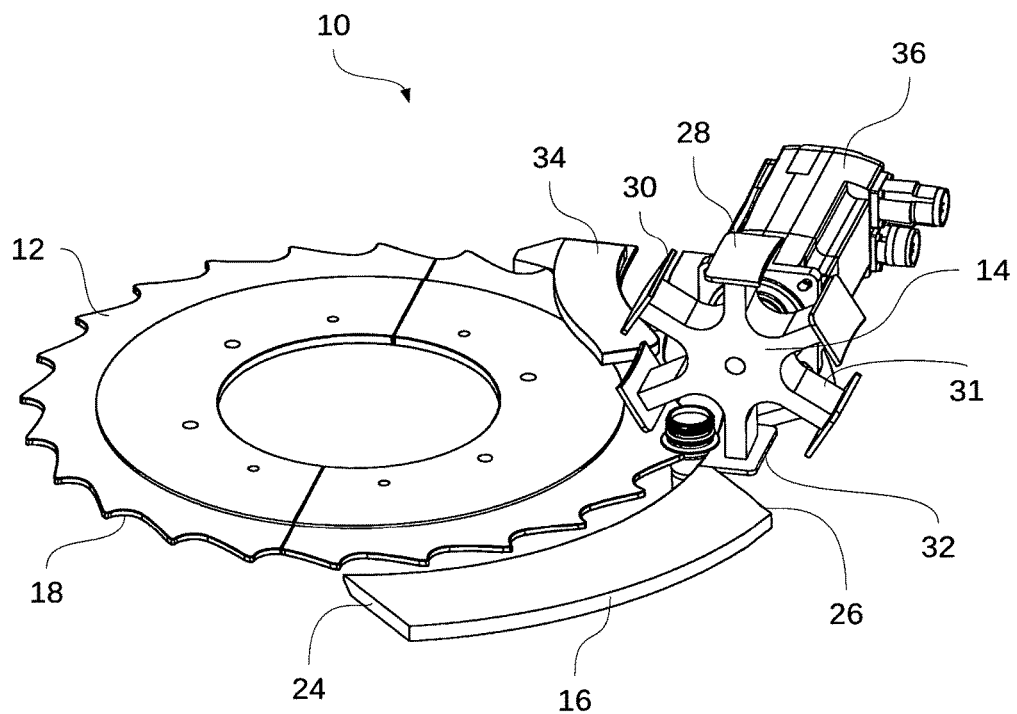

guide collar is radially spaced apart from the transportation wheel, wherein the preforms (20) are transported in suspension between the transportation wheel (12) and the guide collar (16) in the region of the sorting device (10), and a selection unit for selectively removing a respective individual preform (20) transported in one of the accommodating recesses (18) of the transportation wheel (12), wherein the selection unit comprises a pivotable ejecting star (14) with a plurality of ejecting arms (31), which ejecting star, when in the idle position, reaches into the peripheral region of the transportation wheel (12) by means of a first ejecting arm (31) immediately adjacent to the guide collar (16) in the transportation direction of the preforms (20), in such a way that the preforms (20) in the accommodating recesses (18) that are transported past the first ejecting arm (31) are secured against unintentionally falling out, wherein the ejecting star (14), in the event of a rotational motion, pushes an individual preform (20), which is marked for removal, out of one of the accommodating recesses (18) of the transportation wheel (12) by means of a second ejecting arm (32) following after the first ejecting arm (31), and wherein, in a recurring manner after the preform (20) marked for removal has been pushed out, the second ejecting arm (31) takes on the securing of the preforms (20) transported past the second ejecting arm against falling out of the accommodating recesses (18).

15 Claims, 5 Drawing Sheets

(52) U.S. Cl.
CPC ............. *B29C 49/78* (2013.01); *G01N 21/90* (2013.01); *B29C 49/4205* (2013.01); *B29C 49/4252* (2013.01); *G01N 21/9081* (2013.01)

(56) References Cited

FOREIGN PATENT DOCUMENTS

| | | |
|---|---|---|
| DE | 102010028500 A1 | 3/2011 |
| DE | 102010028500 A1 | 11/2011 |
| DE | 102010028905 A1 | 11/2011 |
| DE | 102010028984 A1 | 11/2011 |
| DE | 102012102073 A1 | 9/2013 |
| EP | 2441563 A2 | 4/2012 |
| WO | 2006058512 A2 | 6/2006 |

* cited by examiner

DEVICE AND METHOD FOR TRANSPORTING PREFORMS IN THE REGION OF A BLOW-MOLDING MACHINE

The present invention relates to a sorting device, to a method for transporting preforms to a blow-molding machine for the blow-molding of containers, as well as a transportation device for the feeding of preforms to a blow-molding machine, as well as a blow-molding machine for the blow-molding of containers from a thermoplastic material.

In the forming of containers by means of blowing pressure impact, preforms made of a thermoplastic material, for instance of PET (polyethylene terephthalate) are fed to various processing stations in the region of a blow-molding machine. Typically, such a blow-molding machine features a transportation device for the feeding of preforms to the blow-molding machine, a heating device for thermal conditioning of the preforms, and a blowing station with a blowing device, in the region of which the tempered preforms are expanded by biaxial expansion to a container. The expansion is effected by means of pressurized gas which is introduced into the preform to be expanded.

For an uninterrupted manufacturing process, the blow-molding machine must be continuously supplied with preforms. Typically, the preforms are transported via a so-called preform conveyor to the blow-molding machine. The preform conveyors typically consist of a silo in which the preforms are stored unsorted, of an ascending conveyor for the removal and forwarding of the preforms stored in the silo, of a rolling conveyor downstream from the ascending conveyor for the alignment of the preforms, and a feed rail arranged downstream from the rolling conveyor, by way of which the preforms are fed to the blow-molding machine aligned and in succession. From the feed rail, the preforms are typically transferred to a transportation wheel, by way of which they are transported to a heating region upstream from the blowing station.

After the transfer of the preforms from the feed rail to the transportation wheel, the preforms are typically examined for errors and irregularities, and to remove any preforms determined to be defective or unsuitable for the blowing process from the transportation flow by means of a selection device before conveying them to the heater.

The transportation wheel for the transfer of successive and aligned preforms is typically constructed as a pocket wheel, in which preforms accommodated by the pockets are transported on a circular trajectory, as they are suspended between the transportation wheel and a curved guide collar, which is radially spaced apart from the transportation wheel. Typically, an inspection device is associated with the transportation wheel, which detects preforms that are defective or unsuitable for further processing. It is known that in order to sort out unsuitable preforms, the curved guide collar guiding the preforms by means of the transportation wheel can be moved away from the transportation wheel by way of a swinging motion. The transported preforms that are suspended between the transportation wheel and the guide collar at the time of the swinging motion are ejected by this motion.

In ejection mechanisms of the type described, it is disadvantageous multiple preforms suspended between the guide collar and the transportation wheel are sorted out simultaneously. This means that not only preforms that are unsuitable for further processing are sorted out, but also preforms that are completely intact and well-suited for the production of containers. However, the ejection mechanism described does not only lead to the unnecessary ejection of well-suited preforms, but it also causes a delay in the transportation of the preforms. The swinging motion of the guide collar is an alternating motion, in which the guide collar must first be swung out of an initial position, and then be swung back again after the ejection of the preforms. During this time, no further preforms can be transported by the transportation wheel. The feeding of further preforms to the transportation wheel is typically paused while this swing takes place. In particular at high processing speeds, when multiple preforms are blown into containers every second, time-consuming forward and backward motions of such ejection mechanisms are unsuitable.

Against this background, the task of the present invention is to provide generic methods and devices that support a feed of preforms to a blow-molding machine at high speeds, and at the same time prevent any unintended ejection of preforms that are suitable for further processing.

The task is solved by way of a sorting device with the characteristics disclosed herein, by a method with the characteristics disclosed herein, by a transportation device with the characteristics disclosed herein, and by a blow-molding machine with the characteristics disclosed herein. Advantageous embodiments are also disclosed.

The invention provides a sorting device for the transportation of preforms made of a thermoplastic material in the region of a blow-molding machine for the blow-molding of containers, comprising a transportation wheel which has a plurality of accommodating recesses for accommodating and conveying the preforms, which accommodating recesses are arranged on the circumference of the transportation wheel in such a way that the accommodating recesses are distributed in the circumferential direction, a guide collar which extends circumferentially around the transportation wheel in some regions in such a way that the guide collar is radially spaced apart from the transportation wheel, wherein the preforms are transported in suspension between the transportation wheel and the guide collar in the region of the sorting device, and a selection unit for selectively removing a respective individual preform transported in one of the accommodating recesses of the transportation wheel, wherein the selection unit comprises a pivotable ejecting star with a plurality of ejecting arms, which ejecting star, when in the idle position, reaches into the peripheral region of the transportation wheel by means of a first ejecting arm immediately adjacent to the guide collar in the transportation direction of the preforms in such a way that the preforms in the accommodating recesses that are transported past the first ejecting arm are secured against falling out of the respective accommodating recesses, wherein the ejecting star, in the event of a rotational motion, pushes an individual preform which is marked for removal, out of one of the accommodating recesses of the transportation wheel by means of a second ejecting arm following after the first ejecting arm, and wherein the second ejecting arm, after the preform marked for removal has been pushed out, moves into the position that secures the preforms (20) against falling out.

In a conceivable variant of the sorting device according to the invention, the transportation wheel may be designed as a pocket wheel, with pocket-like accommodation recesses distributed around its circumference, specifically distributed evenly. The invention provides that the accommodation recesses of the transportation wheel the preforms respectively on a shaft area below a support ring of the preform in the transportation position are at least in some regions designed all around.

With the sorting device, individual preforms transported by the transportation wheel may be separated and ejected or removed from the transportation flow. By this is meant that the preforms selected for removal are guided out of the transportation flow, and that they are thus removed from the subsequent process steps for producing a container. It is understood that any number of preforms selected for removal may be consecutively removed from the transportation flow in the sorting device.

This proposed type of sorting of individual preforms has proven to be particularly advantageous for transportation at high processing speeds. Unlike conventionally employed ejection mechanisms in which preforms are separated out of the transportation flow by track switches, by forward and backward-swinging guide collars, or by linearly moving ejectors, the inventive rotating ejection movement by means of an ejecting star is particularly time-saving. The otherwise necessary return movements of back-and-forth moving mechanisms are dispensed with.

Due to the clock-like advance motion of the ejecting star, a single preform marked for removal is ejected each time, while a next ejecting arm is made available immediately for the next preform without a preceding backward motion of the ejecting star. The trailing ejecting arm actively pushes out the preform marked for removal, and after having successfully performed the ejection rotation function, it takes over the function of the first ejecting arm. This ejection movement can be repeated as often as necessary without backward rotations. This leads to an increase in performance of such sorting devices, of related transportation systems, of associated inspection systems, and finally, to an overall performance increase of blow-molding machines.

The guide collar, which is radially spaced apart from the transportation wheel, forms a safeguard preventing the preforms transported in the accommodation recesses of the transportation wheel from falling out of the transportation wheel. The preforms transported by the transportation wheel preferably slide along in suspension from a support ring arranged below arranged below the outflow region on the guide collar. Preferably, the guide collar is arranged at a fixed distance to the circumference of the transportation wheel. The guide collar may be stationary, rigid, or in a fixed position with respect to the transportation wheel.

According to the invention, the ejecting star is pivotable. The ejection mechanism somewhat resembles a revolver, so that for every individual ejection of a preform, the ejecting star preferably rotates by segments, in other words, by a definable angular distance.

In conceivable embodiments, the ejection or removal of an individual preform from the transportation flow may be done actively and/or passively. In case of a passive ejection movement, an ejecting arm of the ejecting star may move away from the transportation wheel in a radially outward direction, thereby removing the safeguard protecting the preform from falling out of an accommodation recess of the transportation wheel. As a result, the preform will fall out of the transportation flow.

In an active version, the ejecting star may forcibly move or push the preform marked for removal out of the accommodation recess of the transportation wheel. One possibility is that an ejection section extending in the rotational direction of the ejecting star may physically contact the preform marked for removal and eject it from the transportation flow.

A passive design is envisioned in particular for sorting devices in which the preforms are transported in free suspension between an edge of the transportation wheel and a guide collar thereto radially spaced apart from it. In this case, the ejecting star supplements the guide collar in a gap, so that the preforms can move forward without interruption when the ejecting star is in an idle position, and fall off the transportation wheel during the rotation of the ejecting star, in particular by force of gravity. Furthermore, in this configuration it is possible the preform marked for removal, when dropping out of the accommodation recess of the transportation wheel, is actively pushed away from the transportation wheel by a subsequent ejecting arm of the ejecting star.

This may improve the safe removal of the preform marked for removal, which is advantageous in particular in case of preforms stuck or jammed on the transportation wheel.

In the design of the transportation wheel, it is also conceivable that the preforms are clamped in place in the accommodation recesses during transportation. In this variant, a guide collar at a radial distance from the transportation wheel can be dispensed with. The accommodation recesses may enclose the preforms in a pincer-like manner, in particular in case of an angular section of more than 180°. In this variant, the active configuration of the ejection mechanism with the rotating ejecting star is particularly advantageous.

In a preferred embodiment, there may be a second guide collar spaced radially to the transportation wheel in the transportation direction of the preforms and immediately after the ejecting star, so that the preforms that are secured against falling out during transportation by the idle ejecting arms are picked up from the ejecting star and moved forward in suspension between the second guide collar and the transportation wheel, at least partially in the circumferential direction of the transportation wheel.

In this embodiment, it was taken into account that a shared guide collar is formed by two guide collar segments, and that the transportation star is arranged in the region of the sorting device such that when it is in idle position, one of the ejecting arms fills a gap between the guide collar segments. When in an idle position, the ejecting arm filling the gap protects the preforms transported in the region of the gap against falling out of their respective accommodation recesses. The preforms can therefore be transported without interruption along the first guide collar segment, past the ejecting arm closing the gap, into the section of the second guide collar segment. With the rotation of the ejecting arm, the gap is opened as a result of the rotational movement of the ejecting arm, and closed again by the subsequent ejecting arm. Thus, a preform located in the region of the gap is guided out of the transportation flow.

The rotation axis of the ejection star and the rotation axis of the transportation wheel may be in planes at an angle to each other. In particular, it was taken into account that the respective axes of rotation of the ejecting star and the transportation wheel are in planes that are perpendicular to each other. Preferably, both the ejecting star and the transportation wheel rotate around respective fixed rotational axes.

A safe ejection of a preform marked for removal is supported by the forcible removal of the preform marked for removal from the accommodation recess by the ejecting star. The forcible removal approximately corresponds to the previously described active configuration of the ejection mechanism. In this embodiment, the preforms marked for removal are moved out of their accommodation recesses in a radially outward direction of the transportation wheel in a particularly jerky movement. In this forcible movement, an arm of the ejecting star captures the preform marked for removal and pushes it mechanically away from the transportation wheel.

In a structurally advantageous embodiment, the ejecting star may have at least three ejecting arms, each of the ejecting arms having a guide segment with a holding section for securing a preform transported in the region of the ejecting star.

As previously explained, a holding section of a guide segment of the ejecting star may secure the preforms guided by the transportation wheel from falling out of their accommodation recesses. For these purposes, the holding section of the guide segment physically contacts the preforms, in particular below a support positioned below their outflow region.

In one variant, it can be provided alternatively or additionally that the ejecting star has at least three ejecting arms, the ejecting arms each having a guide segment with an ejection section for ejecting a preform transported in the region of the ejecting star. As previously explained, an ejection section may serve for the active ejection of a preform located in an accommodation recess of the transportation wheel.

The previously described variants may feature ejecting stars with three, four, five, or six ejecting arms.

For an easy adaptability of the processing speed of the sorting device and for the smooth running of the ejection process when changing from transportation speeds in the region of the sorting device, the rotational movement of the ejection star may be synchronized with the rotational movement of the transportation wheel.

When the rotational movement of the ejecting star is synchronized with that of the transportation wheel, it was particularly contemplated that the rotational speeds of the ejecting star and of the transportation wheel are linearly dependent on each other. This may mean that when increasing the rotational speed of the transportation wheel, the rotational speed of the ejecting star increases in linear proportion when a single preform is ejected. The same applies when the speeds are lowered. Alternatively or additionally, it is also proposed to create a temporary non-linear dependence between the rotational movements. This allows for an at least temporarily accelerated rotation of the ejecting star relative to the transportation wheel, or vice versa.

The synchronization of the rotational movements has advantages in terms of the scalability of the processing speeds. Preferably, the rotational movement of the ejecting star, is clocked with respect to the rotational movement of the transportation wheel. In each cyclic rotation of the ejecting star, the ejecting star is envisioned to rotate along a predefinable angular section.

With respect to the synchronization of the rotational movement, is was particularly contemplated that a rotation of the ejecting star is only possible when there is a preform in the operating section of the ejecting star. This may prevent a premature or delayed release of the ejection mechanism. For this embodiment, it was taken into account that the position of the transportation wheel is registered, and further processed for the purpose of controlling the ejecting star. This may be done by means of a dedicated controller.

In a simple variant, it is contemplated that the rotational movements of the transportation wheel and of the ejecting star are mechanically coupled, for instance by means of a joint transmission. In one possible embodiment, the synchronization may be alternatively or additionally adjustable via an electronic controller.

The invention also relates to a method for supplying preforms to a blow-molding machine for blow molding containers from a thermoplastic material, in which aligned successive preforms are fed to a first separation unit with a sorting device for sorting out individual preforms, in which the preforms are inspected in the region of the separation unit by means of an inspection device, and in which the preforms are then transferred to an accumulation segment for accumulation and/or for filling gaps formed in the course of the separation process.

For a reliable detection of preforms that are defective or unsuitable for further processing, the preforms may be inspected in the sorting device in a contact-free manner, in particular in an optical manner for material irregularities by means of the inspection device.

In the inventive method of feeding preforms, the preforms are lined up and aligned, and transferred to a separation unit. The preforms may be lined up and aligned in the region of a conveyor upstream of the separation unit, in particular by means of a rolling sorter. The first separation unit serves the purpose of probing or processing individual preforms. The accumulation segment downstream from the first separation unit with the sorting device may be embodied as an air conveyor, and/or as an at least partially horizontal feed rail.

For a particularly efficient removal of preforms unsuitable for further transportation or processing, the separation unit may feature a transportation wheel which guides the preforms to the inspection device and then for selective removal to a selection unit of the sorting device, prior to their transfer to the accumulation segment.

When only a single transportation wheel is used, which first transports the preforms into the processing section of the inspection device and then into the processing section of the sorting device or the selecting unit, this supports a particularly compact construction of the blow-molding machine and associated conveyors on the one hand, and it allows for an easily controllable separation of selected preforms, on the other hand. In one transportation wheel, the preforms are respectively guided in individual retaining elements, for example in pocket-shaped accommodation recesses. The inspection device allows for the identification of a preform that should be ejected, and by way of an unambiguous association of that preform with the retaining element, it can be removed at selection unit of the sorting device downstream from the inspection device.

A complex process control is required in particular in case of a separating device with a first transportation wheel, in which a preform marked for removal is identified by inspection devices, and with a second transportation wheel, at which the identified preform is ejected. In such constructions, a control device must monitor the position of a preform marked for removal during its transportation at two separate transportation wheels, and activate the separation unit at a time at which the preform passes the separation unit on the second transportation wheel. It is not only the rotational speeds of the transportation wheels involved which must be synchronized closely, but the movement of the preforms marked for removal during a change of rotation direction and of angular speed must be registered and processed. When a single transportation wheel is used on which the preforms are checked as well as selectively removed, the control effort is significantly lower, and can therefore be implemented in a more reliable and robust manner.

For the further transportation of the preforms in the accumulation segment downstream from the separation unit, the accumulation segment may comprise a conveyor device with a transportation line, along which the preforms are along transported in a substantially horizontal direction. In a first variant, the accumulation segment only consists of the conveyor with the substantially horizontal transportation line. Alternatively, the accumulation segment may at least partially comprise a conveyor device with the substantially horizontally transportation line.

The means of propulsion of the conveyor device featuring the transportation line for transporting the preforms are advantageously chosen so as to support a form transport that is non-destructive to materials. For example, the preforms could be charged with flowing air, the outflow region or a support ring segment of the preforms could be held between suitable clamping means, or roller guides could be used that guide the preforms in a low-friction manner along a predetermined transportation line.

The concept of a horizontal transportation line for the preforms comprises, apart from an exactly horizontal orientation, also light inclines, typically at angles of up to +/−10°, so that relatively few upward or downward inclines would be encountered during transportation. The factual orientation of the substantially horizontal transportation line follows from the interconnected sorting devices and blow-molding machines as well as from the specific assembly heights of components used. In particular, the transportation of the preforms by means of roller guides described below also allows for a very flat configuration of the sorting device with toward the blow-molding machine an upward-sloping transportation line for the preforms. The roller guides are suitable for realizing an upward-sloping transportation line for the preforms up to approx. 30°. Even such an inclining transportation line for the preforms proves to be particularly advantageous in combination with sorting facilities that have rotating disks.

According to an embodiment of the invention already briefly mentioned above, the preforms are transported along the substantially horizontal transportation line by means of a gas flow.

The required gas flow can be provided in a convenient manner in that the propulsive force is generated by a compressed air flow. Specifically, the preforms are moved by air blasts, that is, by means of pulsating pressure air blasts.

An advantageous application of the feed forces results from the fact that the feed force acts on the preforms between a preform outflow region and a support ring.

To avoid contact pressures between the preforms and the guide rails used, it is advantageous that the feed force acts on the preforms from the outside.

For an optimum utilization of flow, it is proposed that the preforms are moved by the gas flow inside a flow channel.

An advantageous power generation in a simple mechanical construction is made possible by having the gas flow in the transportation direction act on the preforms at an angle.

It is conducive to a uniform provision of propulsive forces along the transportation trajectory that the gas flow along the transportation line of the preforms is directed at the preforms from a plurality of outflow openings.

In order to achieve a low overall construction height for the entire device, it proves to be particularly advantageous for the preforms to be transported by the gas flow in a substantially horizontal direction.

An additional mechanical pressure for the transportation of the preforms through the accumulation segment can be obtained by moving the preforms in the region of the accumulation segment in a vertically slanted downward direction.

To support a simple application-dependent configurability of the conveyor, the gas flow can be directed through at least one insert positioned in a guiding device towards the preforms.

In one possible embodiment of the method, one of the previously described sorting devices may be used as a sorting device.

In a further embodiment of the method, the preforms coming from the accumulation segment are transferred to a second separation unit, and transported further separately without gaps after completely successful separation.

When transferring from the accumulation line and the further conveyance of the preforms in the second separation unit, it is ensured that the preforms can be transferred separately without gaps to further processing stations of the blow-molding machine. The closing of gaps is advantageous because this supports an uninterrupted production of the containers in the blow-molding machine.

Advantages and variants of the inventive method also follow, among other things, from the details explained with respect to the sorting device according to the invention.

The invention also relates to a transportation device for the feeding of preforms to a blow-molding machine for blow molding of containers from a thermoplastic material, the blow-molding machine being constructed and adapted to preform one of the previously described methods. In a preferred embodiment of the transportation device, the transportation device comprises one of the previously described sorting devices.

The invention also relates to a blow-molding machine for blow molding containers from a thermoplastic material, the blow-molding machine comprising one of the previously described sorting devices and/or one of the transportation devices described above.

Advantages and preferred embodiments of the inventive transportation device for feeding preforms to a blow-molding machine and of the inventive blow-molding machine also follow from the details given on the inventive sorting device and on the inventive method for the feeding of preforms.

Figure 2:
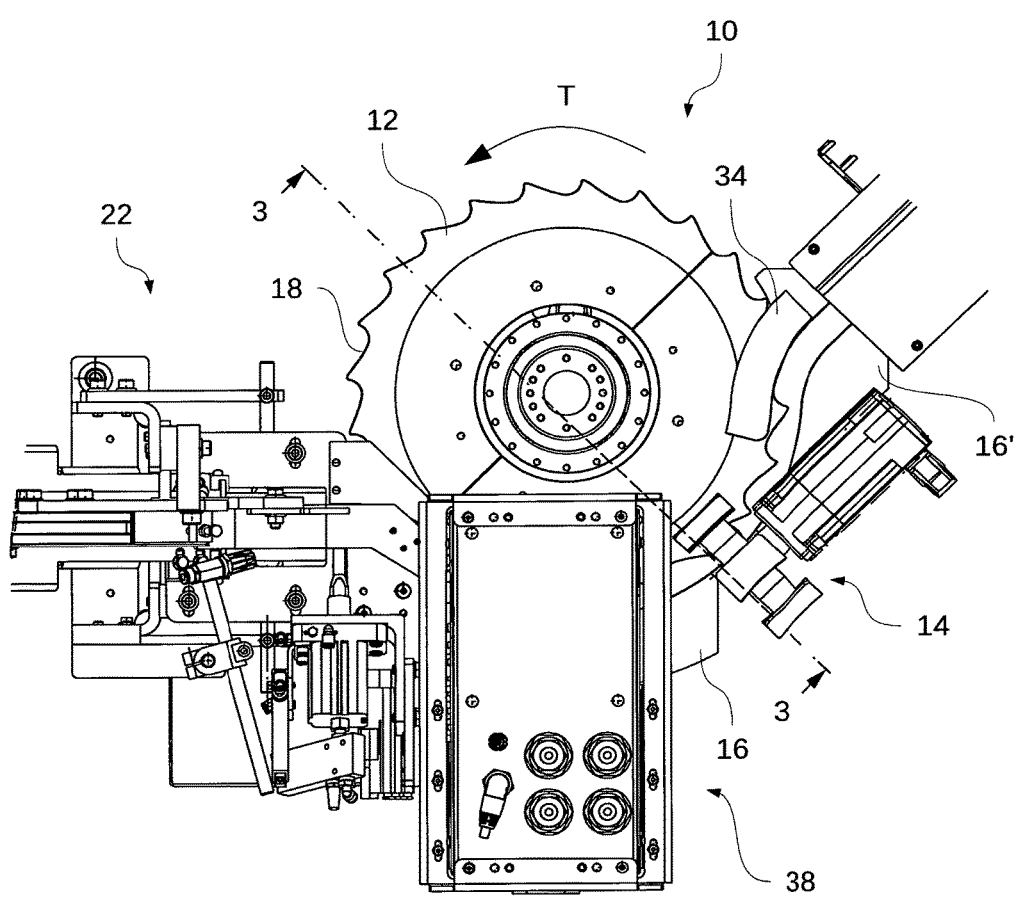
Figure 3:
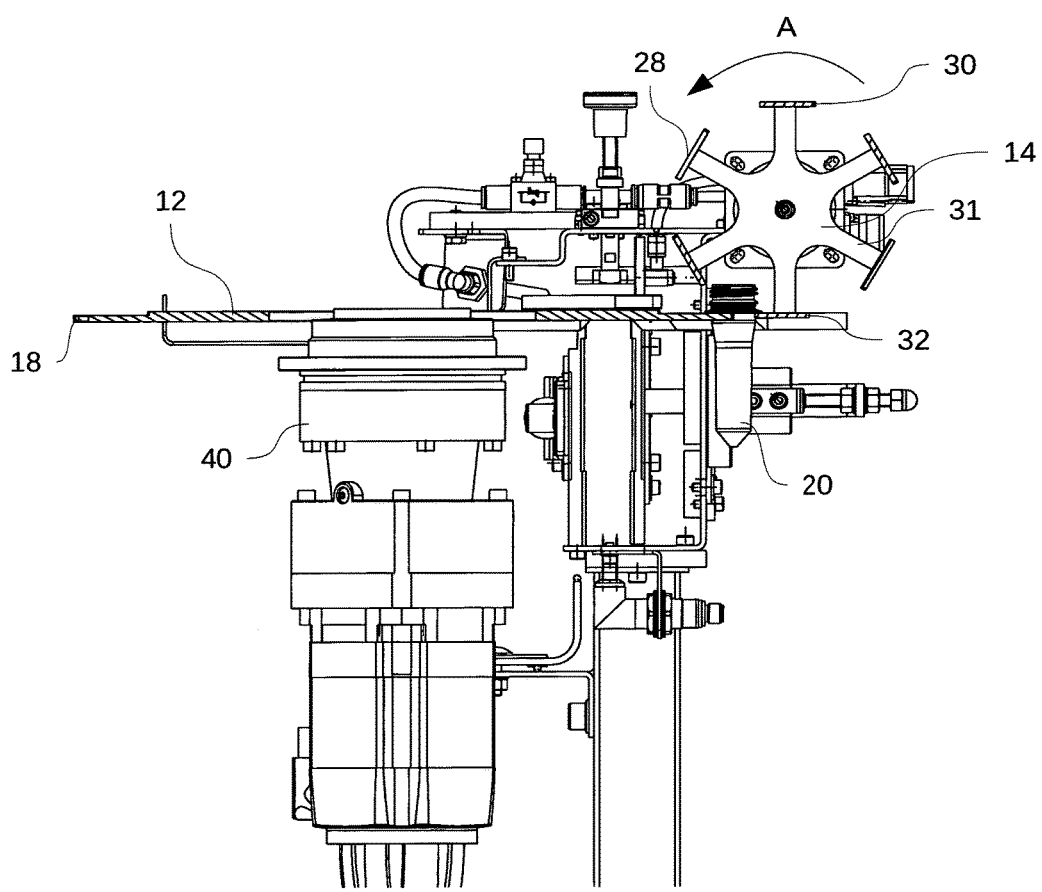
Figure 4:
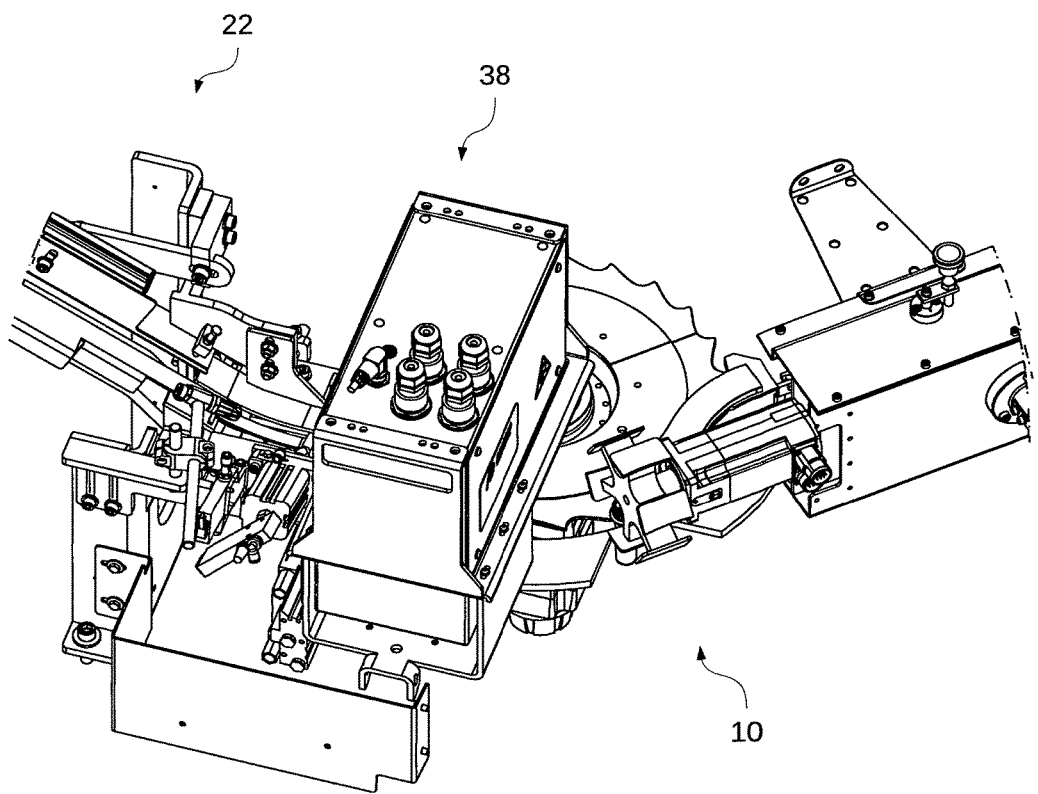
Figure 5:
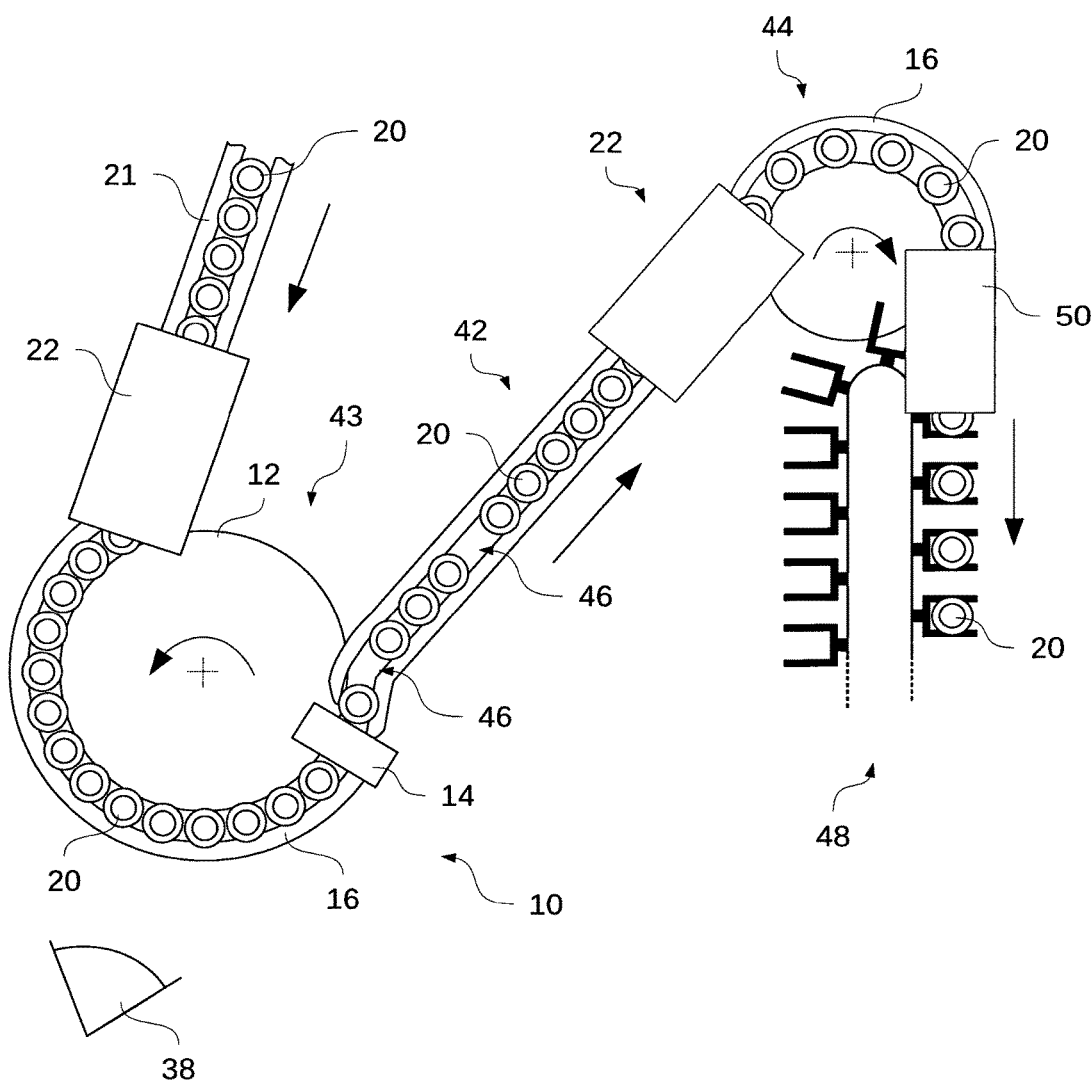

Embodiments of the invention are schematically shown in the drawings:

FIG. 1 shows an isometric view of a sorting device according to the invention,

FIG. 2 shows a top view of the sorting device of FIG. 1 with an inspection device, and a lead-in region, FIG. 3 shows a sectional view of the sorting device of FIG. 2, taken along line 3-3, FIG. 4 shows an isometric view of the sorting device with the inspection device and the inlet area from FIG. 2, and FIG. 5 shows a highly schematic representation of a transportation system with a transportation device according to the invention, an accumulation segment, and a separating device.

FIG. 1 shows an isometric view of a sorting device 10 according to the invention with a transportation wheel 12 rotating in a plane, and with an ejecting star 14 arranged on the perimeter of the transportation wheel 12. The ejecting star 14 is mounted on a rotational axis and rotates in a plane at an angle, or specifically, perpendicularly to the rotation plane of the transportation wheel 12.

In the variant shown, the transportation wheel 12 is sectionally surrounded by a guide collar 16. The transportation wheel 12 has pocket-like accommodation recesses 18, which are designed for accommodating and transporting preforms 20. In the variant shown, preforms 20 are transported in free suspension between the guide collar 16 and the transportation wheel 12 in the circumferential direction of the transportation wheel 12. For that purpose, the preforms 20 are forcibly moved in the direction of rotation of the transportation wheel 12 by trailing edges of the pocket-shaped molded accommodation recesses 18.

The preforms 20 are transferred to the transportation wheel 12 in a lead-in region 22 exemplarily shown in FIGS. 2 and 4, and after this transfer they are transported further in free suspension between the guide collar 16 and the transportation wheel 12 on a retaining collar positioned below their outflow region.

In the variant of the sorting device 10 shown here, the guide collar 16 is embodied as an arc segment, with a trailing edge 24 and a leading edge 26 when viewed in the direction of rotation of the transportation wheel 12. Immediately after the leading edge 26, the guide collar 16 is followed by the ejecting star 14. The ejecting star 14, which rotates in the variant shown in a plane perpendicular to the plane defined by the transportation wheel 12, features ejecting arms 14 with guide segments 28, which are plate-shaped in the variant shown. The guide segments 28 each have a holding section 30 which secures the preforms 20 after their transfer from the guide collar 16 against falling out of the accommodation recess 18 of the transportation wheel 12, and which continues in the variant shown in the circumferential direction of the transportation wheel 12. In the present case, the holding section 30 is approximately collar-shaped, and when it supports the preforms 20 in a idle position, it complements the guide collar 16 in the region of the ejecting star 14.

The guide segment 28 with the holding section 30 is fastened to an ejecting arm 32 of the ejecting star 14. As shown, the guide segment 28 may be formed as a plate which is transversely, or specifically: perpendicularly attached to the ejecting arm 32 in a radial direction. In addition to a holding section 30 which secures the preforms 20 against unintentionally falling out of the accommodation recess 18, the guide segment 28 may also feature an ejection section 32.

When the ejecting star 14 is rotated, the guide segment 28 with the holding section 30 moves outward in a radial direction of the transportation wheel 12, and releases a preform 20 that had previously been secured by the holding section 30 for ejection.

In the illustrated variant, an edge of the ejection section 32 moving in the rotational direction of the ejecting star 14 pushes the preform 20 that was released at the holding section 30 radially outward, away from the transportation wheel 12.

A guide rail 34 arranged downstream from the ejecting star 14 accepts the preforms 20 transported by the transportation wheel 12 and leads them away from the transportation wheel 12 for onward transportation.

FIG. 2 shows a top view of the sorting device 10 of FIG. 1 with an inspection device 38 arranged in the region of the transportation wheel 12 for detecting preforms 20 unsuitable for the blow molding process, and a lead-in region 22 serving for the transfer of the preforms 20 to the transportation wheel 12. In FIG. 2, a second guide collar segment 16' is shown, which is arranged downstream, immediately behind the ejecting star 14, when viewed in the transportation direction of the preforms 20. When the ejecting star 14 is in its idle position, the gap between the guide collar segments 16 and 16' allows for an uninterrupted transportation of preforms 20 from the guide collar segment 16 to the guide collar segment 16' is possible. As long as no ejection of a preform 20 is occurring, the guide segment 28 of the ejecting star 14 with the holding section 30 supports the preforms 20 transported in the accommodation recesses 18—at least in the variant shown here. The gap filled by the ejecting star 14 with the guide segment 28 between the guide collar segments 16 and 16' has at least the width of a preform 20. In particular, the distance between the sections 16 and 16' corresponds at the most to the mean distance between two consecutive accommodation recesses 18 of the transportation wheel 12. The direction of rotation of the transportation wheel 12 envisioned for the transportation of the preforms 20 is shown by the arrow T.

FIG. 3 is a sectional view of the sorting device 10 along the line 3-3 in FIG. 2. The preform 20 is clearly visible, freely suspended between the guide segment 28 of the ejecting star 14 and the peripheral region of the transportation wheel 12 from a retaining collar below the outflow region of the preform 20. As clarified by the sectional view and as can be seen in comparison with FIG. 1, the preform 20 is contacted for the transportation along the transportation wheel 12 by a trailing edge of the accommodation recess 18, and forcibly moved during the rotation of the transportation wheel 12 in the circumferential direction. The direction of rotation of the ejecting star 14 is indicated by the arrow A.

Below the transportation wheel 12, a drive 40 for the transportation wheel 12 is shown. As shown, the transportation wheel drive 40 may be used as a drive or as a supporting mounting for the transportation wheel 12.

As can be clearly seen in FIG. 3, the ejecting star 14 has several ejecting arms 32 which extend radially outward from the axis of rotation of the ejecting star 14. At the end segment of each radially outward oriented ejecting arm 32, a guide segment 28 is arranged with an ejection section 32 extending in the direction of rotation of the ejecting star 14, and with a trailing holding section 30. The ejection section 32 and/or the holding section 30 can each be formed by edges pointing in the circumferential direction of the transportation star 14.

In FIG. 3 it can be clearly seen that for the ejection of a preform 20 through the rotation of the ejecting star 14, first the holding section 30 is directed radially outward and moved away from the transportation wheel following the circular movement of the ejecting arm 32, upon which the preform 20 is ejected by the ejection section 32 of the transportation wheel 12.

FIG. 4 is an isometric view of the sorting device 10 with the inspection device 32 and the lead-in region 22 of FIG. 2.

FIG. 5 shows a highly schematically representation of a transportation device with an inventive sorting device 10. Illustrational details were not shown here for reasons of clarity. In this figure, a lead-in region 22 is shown, in which preforms 20 are transferred, for instance, to a sorting device 10 according to the invention. The lead-in region 22 receives aligned successive preforms from a lead-in rail 21, which is located upstream from the lead-in region 22 in the transportation direction of the preforms 20. Downstream from the lead-in region 22, the preforms 20 are transferred to the transportation wheel 12 of the sorting device 10. The preforms 20 are transported by the rotation of the transportation wheel 12 in the region of the sorting device 10 in the circumferential direction of the transportation wheel 12, in suspended between the transportation wheel 12 and a guide collar 16. The preforms can be accommodated in pocket-shaped recesses on the periphery of the transportation wheel 12 (not shown). Details of the transportation device, in particular of individual components, can be embodied as explained for the preceding figures.

An inspection device 38 inspects the preforms 20 transported on the transportation wheel 12. Upon detection of preforms 20 unsuited for further processing or for further transportation, an inventive ejecting star 14 is controlled such that the preforms 20 identified as unsuitable are individually removed or ejected from the transportation flow of the preforms 20.

When individual preforms 20 are discarded, gaps 46 are formed in the transportation flow, which must be filled before the transfer to the blow-molding machine. In the variant shown here, it is proposed that in order to fill the gaps 46, an accumulation segment 42 be added downstream from the sorting device 10. The accumulation segment may, for instance, be constructed as an air conveyor. In a conceivable alternative, the accumulation segment 42 may be constructed as an at least partially horizontal and/or sloping feed rail. The accumulation segment 42 is followed by a further lead-in region 22, which receives the preforms 20 and transfers them to a separation device 44. Details about a conveyor device used in the accumulation segment may be embodied as described in the documents WO 2006/058512 and/or DE 10 2010 028 500 A1. For configuration details, reference is made expressly to these documents.

By means of the separation device 44, the preforms 20 are separated for further transportation in the region of a blow-molding machine, for instance for being fed into a heating segment. One possibility might be, for instance, that the preforms 20 be transferred to a lead-out region 50 in the region of the separation device 44, in particular of a transportation wheel associated with a separation device, which then transfers the preforms 20 sequentially to an individual conveyor line 48. Details of the shown transportation wheel of the separation device 44 can be embodied like the transportation wheel 12 of the sorting device 10. In the variant shown, there is a purely schematic indication that the individual conveyor line 48 can be embodied as a circulating belt with attached conveyor forks for the transporting of separated preforms 20. In addition, other commonly used conveyor lines for the transportation of individual preforms 20 are conceivable as well.

The transportation device shown here makes it possible to sort out preforms 20 that are identified as unsuitable, and it provides for the closure of the gaps 46 resulting from the removal of preforms 20, so that a continuous and uninterrupted transportation flow of preforms 20 to a blow-molding machine, in particular to a heating device of a blow-molding machine is possible despite the reduced device complexity.

LIST OF REFERENCE NUMBERS

10 Sorting device
12 Transportation wheel
14 Ejecting star
16 Guide collar
18 Accommodation recess
20 Preform
21 Lead-in rail
22 Lead-in region
24 Guide collar trailing edge
26 Guide collar leading edge
28 Guide segment
30 Holding section
31 Ejecting arm
32 Ejection section
34 Guide rail
36 Ejection drive
38 Inspection device
40 Transportation wheel drive
42 Buffer zone
43 First separation unit
44 Second separation unit
46 Gap
48 Individual transportation line
50 Lead-out region
T Rotational direction of the supporting wheel
A Rotational direction of the ejecting star

The invention claimed is:

1. A sorting device for transporting preforms composed of a thermoplastic material in a region of a blow-molding machine for blow-molding the preforms into containers, comprising:
a transportation wheel, which has a plurality of accommodating recesses for accommodating and conveying the preforms, which accommodating recesses are arranged on a circumference of the transportation wheel in such a way that the accommodating recesses are distributed in a circumferential direction;
a guide collar, which extends circumferentially around the transportation wheel in some regions in such a way that the guide collar is radially spaced apart from the transportation wheel, wherein the preforms are transported in suspension between the transportation wheel and the guide collar in the region of the sorting device; and
a selection unit for selectively removing a respective individual preform transported in one of the accommodating recesses of the transportation wheel;
wherein the selection unit comprises a pivotable ejecting star with a plurality of ejecting arms, which ejecting star, when in the idle position, reaches into a peripheral region of the transportation wheel by means of a first ejecting arm immediately adjacent to the guide collar in a transportation direction of the preforms, in such a way that the preforms in the accommodating recesses that are transported past the first ejecting arm are secured against unintentionally falling out of the accommodation recesses, wherein the ejecting star, in the event of a rotational motion, pushes the individual preform, which is marked for removal, out of one of the accommodating recesses of the transportation wheel by means of a second ejecting arm following after the first ejecting arm, and wherein, in a recurring manner after the preform marked for removal has been pushed out, the second ejecting arm secures the preforms transported past the second ejecting arm against falling out.

2. The sorting device according to claim 1, wherein in the transportation direction of the preforms, immediately adjacent to the ejecting star, a second guide collar is spaced radially from the transportation wheel, such that the preforms that are secured during transportation against falling out by the idle ejecting arms are received from the ejecting star, and are transported further in suspension between the second guide collar and the transportation wheel in suspension, at least partially in the circumferential direction of the transportation wheel.

3. The sorting device according to claim 1, wherein an axis of rotation of the ejecting star and an axis of rotation of the transportation wheel lie in planes that are at an angle with respect to each other.

4. The sorting device according to claim 1, wherein the ejecting star has at least three ejecting arms, wherein each of said at least three ejecting arms has a guide segment with a holding section for securing one of said preforms transported in the holding section of said ejecting star.

5. The sorting device according to claim 1, wherein the ejecting star has at least three ejecting arms, wherein each of said at least three ejecting arms has a guide segment with an ejection section for ejecting one of said preforms transported in the ejection section of said ejecting star.

6. The sorting device according to claim 1, wherein rotational movement of the ejecting star is synchronized with rotational movement of the transportation wheel.

7. A method for feeding preforms composed of a thermoplastic material to a blow-molding machine for blow molding the preforms into containers, the method comprising:
   transferring lined up and aligned preforms to a first separation unit having a sorting device according to claim 1;
   inspecting the preforms in the first separation unit by means of an inspection device and selectively removing respective individual preforms from the first separation unit that do not pass inspection using the selection unit of the sorting device; and
   subsequently transferring non-removed preforms from the first separation unit to an accumulation segment configured to hold and/or to close gaps resulting from removals of preforms.

8. The method according to claim 7, wherein the first separation unit comprises the transportation wheel of the sorting device, wherein the transportation wheel transfers the preforms to the inspection device and then to a selection unit of the sorting device for selective removal, prior to the subsequent transfer of the preforms to the accumulation segment.

9. The method according to claim 7, wherein the accumulation segment comprises a conveyor having a transportation line, and wherein the preforms are transported along the transportation line in a substantially horizontal direction.

10. The method according to claim 7, wherein a feed force for transportation of the preforms along the accumulation segment is generated by means of compressed air flow.

11. The method according to claim 7, wherein the preforms in the region of the sorting device are inspected by means of the inspection device contactlessly for material irregularities.

12. The method according to claim 7, wherein preforms exiting the accumulation segment are transferred to a second separation unit and transported individually without gaps after successful separation.

13. A transportation device for feeding preforms to a blow-molding machine for blow molding containers made from thermoplastic material, said transportation device comprising:
   a sorting device according to claim 1 configured to transfer lined up and aligned preforms to a first separation unit;
   an inspection device for inspecting preforms in the first separation unit; and
   an accumulation segment configured receive the preforms transferred from the first separation unit and to hold and/or close gaps resulting from removals of preforms in the first separation unit.

14. A blow-molding machine for blow molding containers from preforms made of a thermoplastic material into containers, said blow-molding machine comprising a transportation device according to claim 13, a heating device for thermal conditioning of the preforms, and a blowing station with a blowing device.

15. The method according to claim 11, wherein contactless inspection of the preforms for material irregularities is performed optically in the region of the sorting device.

* * * * *